United States Patent [19]

Hirschfeld et al.

[11] Patent Number: 4,791,940

[45] Date of Patent: Dec. 20, 1988

[54] ELECTRONIC PERIODONTAL PROBE WITH A CONSTANT FORCE APPLIER

[75] Inventors: John W. Hirschfeld; Charles H. Gibbs; James G. Lee, all of Gainesville, Fla.

[73] Assignee: Florida Probe Corporation, Gainesville, Fla.

[21] Appl. No.: 9,523

[22] Filed: Feb. 2, 1987

[51] Int. Cl.⁴ .............................................. A61B 5/10
[52] U.S. Cl. ..................... 128/776; 128/777; 33/169 B; 33/513; 433/72; 433/141
[58] Field of Search ............. 128/776, 777; 33/169 B, 33/513, 514; 433/72, 141

[56] References Cited

U.S. PATENT DOCUMENTS 4,203,223  5/1980  Lautenschlager ............... 433/141
4,665,621  5/1987  Ackerman ........................ 33/513

Primary Examiner—Edward M. Coven
Assistant Examiner—Randy Citrin
Attorney, Agent, or Firm—John B. Dickman, III

[57] ABSTRACT

A periodontal probe and recording apparatus for measuring the depth of a pocket formed by the gum (gingival tissue) surrounding a tooth. The periodontal probe and recording apparatus are comprised of a probe tip with a simplified spring tension device electrically connected via a transducer to the recording apparatus. The probe tip reciprocates via a movable arm in a short, easy to clean, sleeve fixed to a probe handle, wherein the probe tip acts against a constant spring tension. With the probe tip resting on the bottom of the pocket, the periodontal probe handle is pressed toward the pocket until the sleeve touches the margin of the gum forming the pocket. The exposed length of the probe tip represents the depth of the pocket. There is a locking mechanism for locking the tip at the measured depth for visual measurement. Also, the probe depth is electronically measured by the mechanical displacement of the transducer and transmitted, at the touch of a foot switch, from the transducer to the recording apparatus comprised of a digital readout and/or a computer with a printer and a voice synthesizer and voice recognition circuits.

13 Claims, 4 Drawing Sheets

ELECTRONIC PERIODONTAL PROBE WITH A CONSTANT FORCE APPLIER

BACKGROUND OF THE INVENTION

This invention relates to a depth-measuring periodontal probe and recording apparatus of the type used by dentists to measure the depth of the pocket between the gum and the tooth. The depth of the pocket also known as gingeval sulcus, is measured from the margin of the gum (the top of the gum) to the epithelial attachment (the point where the gum attaches to the tooth), which forms the bottom of the pocket. Measurement of pocket depth is a primary method for detecting periodontal (gum) disease. Peridontal disease is commonly known as pyorrhea. It has been estimated that most adult tooth loss in the United States today is the result of peridontal disease, not dental caries (cavities). As peridontal disease progresses, the pockets become larger and are filled with bacteria and pus, and in time, destruction of the tissue attachment to the teeth and destruction of the supporting bone structure occurs. Periodontal disease is usually painless, site specific and goes through periods of exacerbation and remission, therefore, an improved, easy to use and record producing periodontal probe and apparatus is a much needed tool in the dental field.

It is common knowledge that early detection and periodic measurements at several locations, as many as six per tooth, is necessary to determine if the gingival sulcus (pocket) is enlarging and how fast. There are many instruments used to measure and record the depth of the pocket such as the Ward Periodontal probe, U.S. Pat. No. 3,058,225, which has a handle with a protruding sleeve and flexible probe tip that connects directly to a mechanical indicator or indirectly to an electric current indication device located on the probe handle. There are disadvantages with this type of probe. The sleeve is long and difficult to keep clean. Blood and other body fluids can create deposits inside the sleeve, which can interfere with the smooth movement of the probe tip. These deposits tend to become hardened and more of a problem following heating precedures of sterilization. Therefore, it is important that any sleeve be kept short, open and easy to clean. Since the dentist makes all measurements by taking his eyes off the tip and observing the indicator, time is lost to observe a measurement. Since there are as many as six measurements per tooth, and the normal mouth has as many as thirty-two teeth, the time lost in taking as many as 192 separate measurements is considerable. Another disadvantage is that probing force is not controlled.

Another prior art periodontal probe is disclosed in Grenfell et al, U.S. Pat. No. 3,943,914, which includes a remote recording console, electrically connected to this probe to provide a permanent record of the depth of the gingival sulci around the particular tooth. The major disadvantage with this type of probe is the long sleeve, which is difficult to keep clean. Probing force is not controlled, which is another disadvantage.

There are commercially available periodontal probes, for example, The Vine Valley Research Corp., sells a unit which sounds a "beep" when a preset probing force is reached. The unit, developed by Dr. Ronald N. Yeaple, U.S. Pat. No. 4,340,069, does not electronically measure pocket depth, only probing pressure. Also, the Oratronics, Inc., sells a unit which consists of a tip which slides within a plastic sleeve, and digital readout and a printer. The long plastic sleeve is difficult to keep clean and tip movement can become restricted.

A published articles in *The Journal of Periodontology*, 1980, Vol. 51, No. 5, pp. 298-300, "A Periodontal probe that Measures to One Tenth Millimeter", by S. G. Detsch, discusses a probe with a mechanical readout on the handle. It utilized a caliper attached to a probe tip. The probe tip slides within a curved sleeve. This probe does not control force and does not provide electronic readout. The curved sleeve is long and difficult to keep clean.

An article by U. van der Velden and J. K. de Vries that appeared in *The Journal of Clinical Periodontology*, 1978, Vol. 5, pp. 188-197, entitled. "Introduction to a New Periodontal Probe: The Pressure Probe", discusses the use of air pressure to extend the probe tip which slides within a sleeve. During probing, the tip will intrude from the position of maximum extension at a force determined by the present pressure, until the metal sleeve contacts the gum margin. The pocket depth is read from a millimeter scale on the handle. The probe does not have a remote readout and the use of air pressure requires a machine unit that is expensive to produce. The sleeve is long and difficult to keep clean.

Lautenschlager et al, in U.S. Pat. No. 4,203,223, described a periodontal probe, which provided a constant force. The sleeve was relatively short, which is advantageous for cleaning. However, there was no provision for electronic measurement. Pocket depths must be read visually as with common probes.

Recently, Ackerman et al, in U.S. Pat. No. 4,665,621 described a periodontal probe with frictional means for limiting probing force, electronic measurement and a microcomputer for analyzing and displaying the data. This probe has a long, curved sleeve, which is difficult to clean. The curved portion of the sleeve adds friction during movement. The probe tip is extended into the gingival sulcus by pressing a control sleeve, which is not convenient to use because it is difficult to simultaneously slide a sleeve and position the probe tip in the gingival sulcus.

A serious handicap of clinical studies and clinical treatment has been the lack of an objective means of measuring progression of periodontal disease. One of the methods periodontists use to diagnose and assess the progression of the disease is tissue attachment level and bone loss by the measure of periodontal pocket depth. Pocket depth is measured with a probe and because there is not a controlled, standardized way of probing, it is only a crude measurement. There is a critical need for a reliable technique for making rapid, accurate measurements in a standardized fashion. The periodontal probe of this invention overcomes the objections of the prior art and is an improvement over standard probes in that it maintains a constant probing force, can record pocket depths distal to posterior teeth accurately (remote readout), provides electronic measurements for computer recording of the data, and is easy to keep clean and operating smoothly without frictional forces coming from a gummed up, dirty sleeve.

SUMMARY OF THE PRESENT INVENTION

The present invention is directed to a periodontal probe and recording apparatus for simultaneously measuring and remotely recording the depth of the periodontal pocket (gingival sulcus) and more particularly, to a unit employing a periodontal depth probe electrically connected to a remote recording device, capable of producing a permanent visual record of the pocket depth being measured. The probe has an elongated body with a movable probe tip, an electronic displacement transducer with digital readout removably attached to the probe body and an electrical cable extending from the electronic digital readout to a remote recording apparatus. Affixed to the probe tip end of the handle is a stationary sleeve through which the tip reciprocates. Connected to the probe tip is an adjustable spring tension device with gram settings for applying a selected constant force to the tip.

By using a probe with a movable probe tip under a constant force, the force applied to the bottom of the periodontal pocket will not become excessive or too little as with other prior art designs. With the present invention, the probing force is preset before the probe tip is inserted in the pocket. When the tip touches the bottom of the pocket, force is applied to the tip as the sleeve slides over the shaft of the tip to contact the margin of the gum. The amount of force is controlled by a spring in the handle of the probe.

The probe is removable and can be detached from the electronic displacement transducer with digital readout for sterilization after each use. While the probe is being sterilized, another sterile probe can be attached and the system can continue to be used. In this manner, a single remote recording apparatus can be used to measure the periodontal pockets of more than one patient with a minimum of delay between each patient.

The electrical cable from the digital readout is of the multi-conductor type for connecting to a computer, for a permanent visual record. Connected to the recorder control circuit of the computer is an operator-controlled foot switch which is depressed by the probe operator each time it is desired to record the pocket depth being measured by the probe. A record is made each time the foot pedal is depressed. Therefore, an accurate measurement can be obtained without the operator having to lose eye contact with the teeth or having to hand-record each measurement or having to employ an assistant to do so.

It is therefore a primary object of the present invention to provide an apparatus for simultaneously and automatically creating a permanent and visual record of the depth of each periodontal pocket as it is measured.

It is a further objective of the present invention to provide a probe tip with an adjustable means for selecting a constant force which reacts against a force applied to the probe.

A further object of the present invention is to provide a periodontal probe and recording apparatus which can be used by a single unassisted operator.

Still another objective of the present invention is to provide a periodontal probe with a removable displacement transducer so that the displacement transducer can be removed during sterilization of the probe.

It is a further objective of the present invention to provide a periodontal probe which has a constant force spring capable of adjustments where the adjustment is completed by a simple, inexpensive means.

A further objective of the present invention is to provide a stationary sleeve (through which the tip reciprocates) which is short and accessible for ease of cleaning.

A further objective of the present invention is to provide a locking button for occasionally locking the probe tip to the handle for improved tactile sense and to allow the dentist to probe at forces greater than the force provided by the spring.

A further objective of the present invention is to provide voice recognition circuits in the recording apparatus (computer) to allow an unassisted operator to control the system fully or partially without the aid of a keyboard or foot switch . . . similarly, voice synthesizer circuits in the recording apparatus (computer) would provide an unassisted operator verbal directions as to which site is to be probed next, etc. without having to lose eye contact with the teeth or touch a non-sterile keyboard.

The foregoing objectives are not stated in an order of importance and there may be other objectives and advantages of equal importance not stated that will become apparent from the following detailed description of the invention taken in conjunction with the accompanying drawings.

BRIEF DESCRIPTION OF THE DRAWINGS

FIG. 3a is a partial cross-sectional view of the periodontal tip and sleeve of the periodontal probe of FIG. 1 taken along the line 3a—3a.

DESCRIPTION OF THE PRESENT INVENTION

Figure 1:
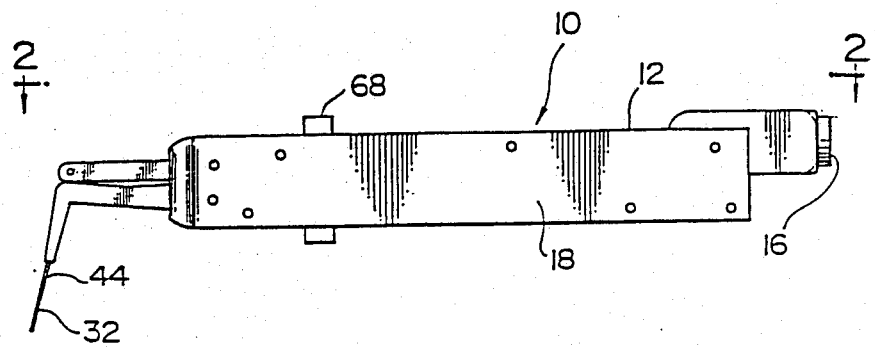
FIG. 1 is a side elevation view of an illustrative embodiment of the periodontal depth probe of the present invention.

Referring to the drawings, there is shown in FIGS. 1–3a and 5, an instrument embodying the periodontal probe of the present invention. FIG. 1 shows a periodontal probe 10 consisting of a body 12 having at one end a probe tip 32 and a coupling 16 at the other end, which connects to a electronic displacement transducer with digital readout (not shown). Looking at FIG. 3, the cover 18 of FIGS. 1 and 2 has been removed to expose the interior of the periodontal probe 10. The body 12 has a cavity 20 with an open end 22.

The cavity 20 is divided into sections 24 and 26. Cavity section 24 contains the working components of the probe tip, including a flat (leaf type) spring 28. A rod 30 reciprocates in cavity section 26 to hold the probe tip against movement, to apply a spring force and to actuate a displacement transducer. The coupling 16 is a continuation of cavity section 26 and is a larger bore than the cavity section 26 in order to contain and support a displacement transducer, not shown, which connects to an electrical cable.

Figure 2:
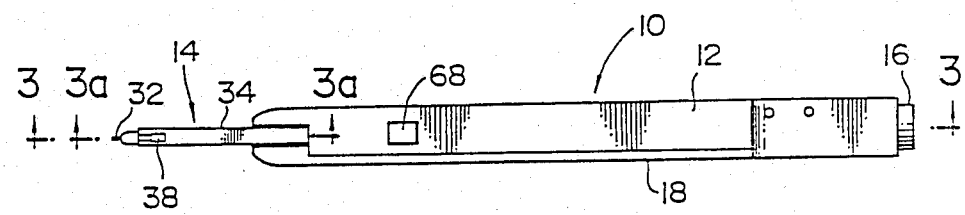
FIG. 2 is a top elevation view of the periodontal depth probe of FIG. 1 taken along the line 2—2.
Figure 3:
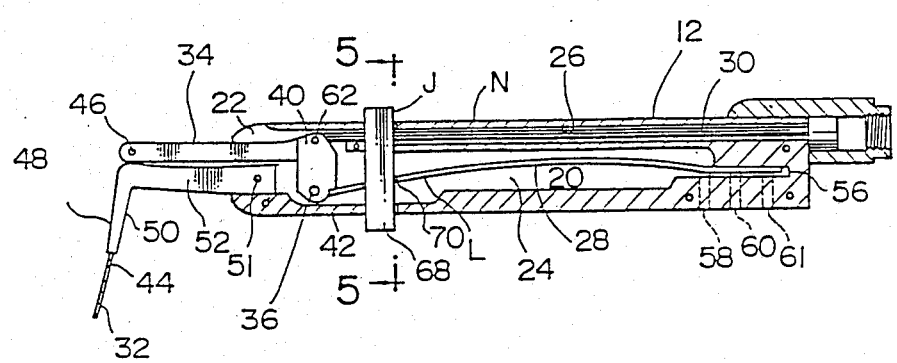
FIG. 3 is a side cross-sectional view of the periodontal probe of FIG. 1 taken along the line 3—3.
Figure 3A:
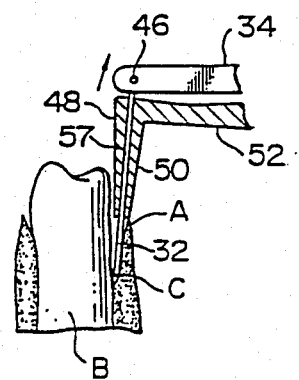
Figure 4:
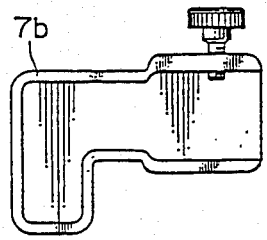
FIG. 4 is a sectional view illustrating a protective cover for the sleeve and probe tip of the periodontal probe of FIG. 1.
Figure 5:
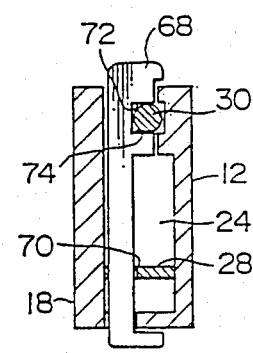
FIG. 5 is a cross-sectional view of the body of the periodontal probe of FIGS. 1 and 3 showing the locking button for locking the probe tip against movement.

The probe end 14 of FIG. 3 has a tapered probe tip 32 pivotally attached to a movable arm 34. In FIG. 2, movable arm 34 has a slotted end 38 in which the probe tip 32 is pivotally attached by a pin 46. The movable arm 34 is pivotally connected to the probe body 12 at pin 36.

The probe tip 32 has graduation marks 44 in millimeters. The pivotal end of the tip 32, not shown, has a circular loop which connects to slotted end 38 by a pin 46. The tip 32 is similar to tips used in common periodontal probes.

The probe tip 32 is guided by a sleeve 48. Sleeve 48 has a tapered conical end 50 and is part of a fixed arm 52 fixed to body 12 at 54. Conical end 50 of the sleeve has a center bore 57 (FIG. 3a) for guiding the tip 32. As pressure is applied to the end of tip 32 at 52, it slides upwardly in sleeve 48 moving upper arm 34 against the constant force of spring device 28. The notch 42 on the movable arm 34 bears against the free end of leaf spring 28 thereby forcing the movable arm 34 to expose the full length of the graduations 44 of probe tip 32, in the relaxed position.

Leaf spring 28 is fastened at one end in a slot 56 in the rear portion of cavity section 24. Set screws 60 and 61 hold the spring in place in the slot 56 of the body 12. The set screw 58 makes fine adjustments to the probing force applied to the probe tip 32.

Figure 6:
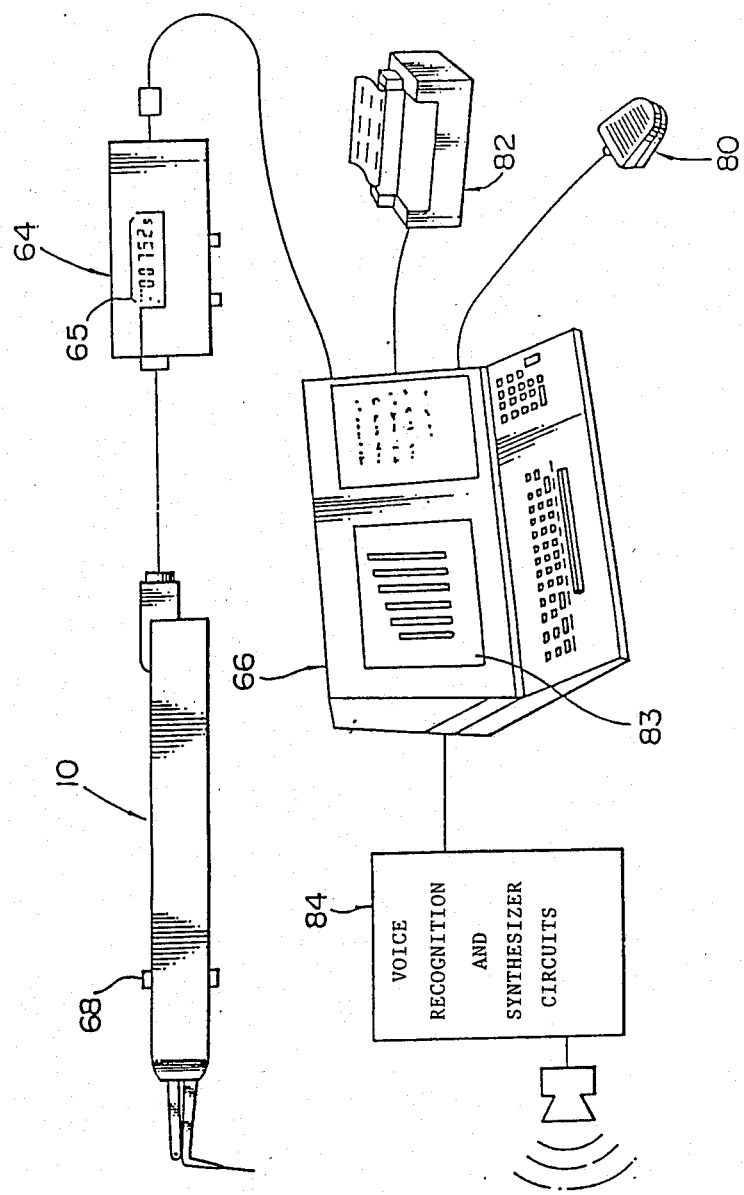
FIG. 6 is a perspective view of an illustrative embodiment of the periodontal depth probe and remote displacement transducer with readout and recording computer apparatus of the present invention.

The rod 30 is pivotally connected at one end to the movable arm 34 at 62. The other end of rod 30 has a cylinder shaped element for mechanically acting on the displacement (FIG. 6) transducer 64 (FIG. 6)to produce electrical signals which control a digital readout 65 and which can be transmitted through an electrical cable to computer 66.

Displacement transducers are commercially available for converting the mechanical displacement of rod 30 into an electrical signal for entry to computer 66. The linear variable differential transformer (LVDT), potentiometer and optical encoder are three common types of displacement transducers, which could be used by someone skilled in the art. A housing would be constructed to support the displacement transducer and a means provided to attach it to coupling 16 at the end of the probe body 12. A means would be provided to connect rod 30 to the displacement transducer such that movement of rod 30 would activate the displacement transducer. The output of the displacement transducer would be connected to a computer interface. A foot switch would also be connected to the computer interface and when pressed would cause the electrical signal from the displacement transducer to be recorded to the computer.

A displacement transducer, which has been used with the present periodontal probe 10, is a non-contact capacitive system 65, with a digital readout 65. This displacement transducer system is sold by the Fred V. Fowler Company of Newton, Mass. as part of a digital caliper known as the Fowler Sylvac Ultra Cal 2, Model No. 54-100-106. This transducer system was removed from the caliper, supported in a housing, the housing attached to coupling 16, and the transducer placed in contact with rod 30. For entry of the electronic signals of this transducer to computer 66, using foot switch 80, the Fowler RS232-C computer interface Model No. 54-118-000 has been used. Adapting a displacement transducer to measure the movements of rod 30 and interfacing the displacement transducer to a computer are obvious to persons skilled in the art. The rod 30 is locked against movement by reciprocating lock button 68, FIG. 5. Button 68 reciprocates vertically in body 12. By pressing down or up on the button 68, the rod 30 is pushed against the wall of cavity section 26, locking movable arm 34 and probe tip 32 against movement. The shape of button 68 includes an upper rest 72 and lower rest 74 for engaging and holding rod 30 against the cavity walls. So that the button 68 does not interfere with the operation of leaf spring 28, the spring has a cutout 70.

In operation, fine adjustment of probing force can be made by loosening or tightening set screw 58. A preset probing force from 10 to 75 grams is possible by using thicker or thinner leaf springs. Set screws 60, 61 secure spring 28 to slot 56 in body 12.

Figure 7:
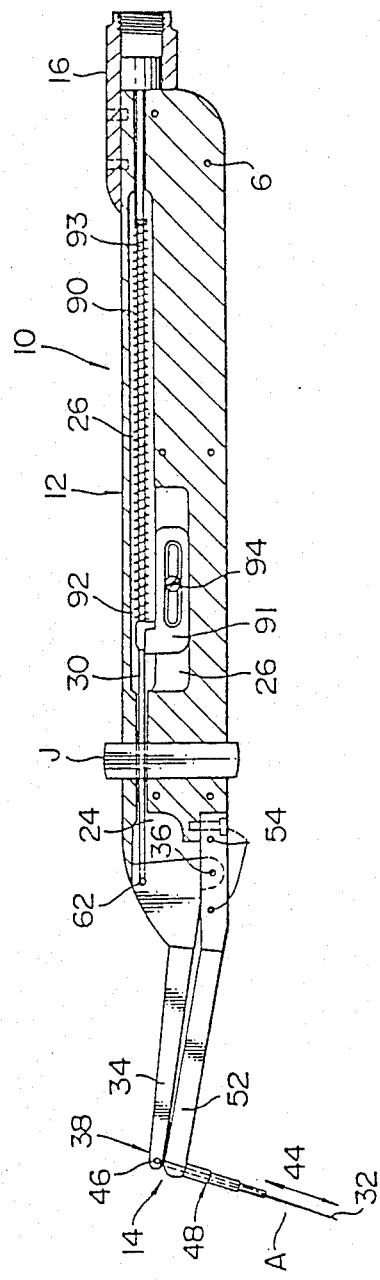
FIG. 7 is a side cross-sectional view of the periodontal probe which utilizes a coil spring (preferred embodiment).

A second, preferred embodiment, of the periodontal probe 10 is shown in FIG. 7. This embodiment differs from the first one shown in FIGS. 1-5, in the method of applying spring force to the probe tip wire 32. The flat spring 28 has been deleted ad a coil spring 90 which surrounds rod 30 has been added. One end of the coil spring 90 is attached to the rod 30 at a threaded enlargement 93. The other end of coil spring 90 is attached to an adjusting block 91 on its threaded portion 92. The tension in coil spring 90 can be varied by moving the adjusting block 91 horizontally in cavity 26 of the body 12. The adjusting block 91 can be secured to the handle 12 with lock screw 94.

In operation, fine adjustment of probing force can be made by loosening lock screw 94 and sliding the adjustment block 91 toward the tip 32 to increase probing force or toward the coupling 16 to decrease probing force. The lock screw 94 is tightened at the desired probing force, securing the adjusting block 91 rigidly to the body 12. A preset probing force from 10 to 75 grams is possible depending upon the wire size of the coil spring. The tension in coil spring 90 applies a force on rod 30 tending to move it toward the tip 32. This force is transmitted to the movable arm 34 through pivot joint 62, tending to rotate movable arm 34 counterclockwise about the body 12 around pivot 36. The spring force is transmitted to the tip 32 through pivot 46 tending to move probe tip 32 downward through sleeve 48.

In operation a protector cover 7b (FIG. 4) is removed from the periodontal probe 10 exposing the probe end 14. The displacement transducer 64 is screwed in to the coupling 16 and the cable is connected between the transducer 64 and the computer 66. The probe tip 32 is placed at the bottom of the periodontal pocket C, in FIG. 3a, between tooth B and gum A. Then sleeve 48 is pushed down, in the direction of the pocket, against the tension of the preset probing force, until the lower end of the sleeve 48, the conical end 50, contacts the margin of the gum A. The pocket depth is visually observable on digital readout 65 and permanently recorded on computer 66 when foot pedal 80 is pushed. Electrically connected to the computer 66 is a printer 82. Audio sounds from the computer via a tone generator or a voice synthesizer 84 can also be incorporated into the computer to remind and assure the dentist that he is probing in the correct sequence. Voice recognition circuits 84 can be installed in the computer to allow the operator to make voice commands to the computer. Voice recognition, synthesizer electronics and software 84 for use with computers for this purpose are commercially available. The "Voice Card for IBM PC and Compatibles" Model VPC 2100 from the Votan Company of Fremont, Calif., USA is one example. Another example is the "Introvoice 5—Voice Recognition Board" from the Voice Connection Company of Irvine, Calif., USA. The dentist may lock the probe tip wire 32 to the body 12 by pushing the lock button 68. Pushing down from the top is usually used during probing of the lower jaw and pushing up from the bottom during probing of the upper jaw. With the probe tip wire 32 locked to the handle, the dentist can feel and probe the pocket as he would with common probes.

Another feature of this device is that lock button 68 allows the dentist to remove the tip 32 from the pocket and visually read the measurement by observing the end of the tip in relation to sleeve 50 and reading the graduations 44. The periodontal probe could be equipped with a fiber optic illuminating system to increase light to the tip area.

In a complete examination, six points on each tooth would be probed. A patient with all thirty-two teeth requires a total of 192 pocket depth recordations. The probing order is preselected on the computer 66 so that the data are labeled properly. Missing teeth are accounted for by the computer. A visual picture on the computer screen 83 reminds the dentist which point should be probed next. The computer can be programmed to back up and to move ahead in the sequence so that corrections can be made. It is also possible to make a continuous plot of the pocket depth by sliding the probe tip at a uniform rate along the floor of the pocket while the depth is recorded on a time base plot.

The pocket depth data are stored on hard and/or floppy disks by the computer and a hard copy for the patient's file (chart) can be printed if desired. The stored data are available for recall to compare with later probings to monitor the patient's changes in status over many years.

The terms and expressions which have been employed in the foregoing abstract and specification are used therein as terms of description and not of limitation, and there is no intention, in the use of such terms and expressions, of excluding equivalents of the features shown and described, or portions thereof, it being recognized that the scope of the invention is defined and limited only by the claims which follow.

We claim:

1. A periodontal depth probe for measuring pocket depth comprising:
   (a) a probe body;
   (b) a rigid probe tip for insertion into the periodontal pocket, which is pivotally connected to a movable arm, where said movable arm is pivotally connected to the probe body; and
   (c) a sleeve partially ensheathing said probe tip said sleeve being fixed to said probe body, the probe tip being reciprocable in the bore in said sleeve.

2. The periodontal probe of claim 1 where said movable arm includes a pivot joint to which a rod is pivotally connected, said rod is guided by a groove in the probe body and reciprocates in this groove when the probe tip reciprocates in its ensheathing sleeve.

3. The periodontal probe of claim 2 where said probe includes a spring attached to the rod for applying a force to the probe tip.

4. The periodontal probe of claim 3 where said spring is a coil spring, which surrounds said rod and is connected to said rod at one end and connected to the probe body at the other end.

5. The periodontal probe of claim 3, where said probe includes a means for locking the probe tip to the probe body.

6. The periodontal probe of claim 5 where said locking means includes a locking button which, when activated, presses the rod against the probe body, frictionally locking the rod to the probe body.

7. The periodontal probe of claim 2 wherein said probe includes a displacement transducer for converting the reciprocating movement of said probe tip relative to said sleeve into an electrical signal representing the depth of said pocket.

8. The periodontal probe of claim 7 wherein said probe includes means for converting said signal into a permanent record and a visual display of pocket depths.

9. The periodontal probe of claim 7 wherein there is a means for actuating said signal on command to produce said record of said depth.

10. The periodontal probe of claim 9 wherein said means for actuating said signal is a foot switch.

11. The periodontal probe of claim 9 wherein said means for actuating said signal includes a voice recognition circuit.

12. The periodontal probe of claim 1 where said probe includes a spring attached to the movable arm for applying a force to the probe tip to allow said probe to reciprocate within said sleeve against a preset force.

13. The periodontal probe of claim 12 where said spring is a leaf spring attached to the probe body at one end and to the movable arm at the other end.

* * * * *